United States Patent [19]

Drake

[11] Patent Number: 4,538,920
[45] Date of Patent: Sep. 3, 1985

[54] STATIC MIXING DEVICE

[75] Inventor: Gerald E. Drake, Knapp, Wis.

[73] Assignee: Minnesota Mining and Manufacturing Company, St. Paul, Minn.

[21] Appl. No.: 471,834

[22] Filed: Mar. 3, 1983

[51] Int. Cl.³ .............................................. B01F 15/02
[52] U.S. Cl. .................................... 366/177; 222/137; 222/145; 366/339
[58] Field of Search ............... 366/336, 337, 338, 339, 366/340, 130, 177, 184, 186, 190, 182, 189; 222/386, 145, 94, 137; 403/348

[56] References Cited

U.S. PATENT DOCUMENTS

| 3,286,992 | 11/1966 | Armeniades et al. | 259/4 |
| 3,635,444 | 1/1972 | Potter | 366/339 |
| 3,664,638 | 5/1972 | Grout et al. | 259/4 |
| 3,862,022 | 1/1975 | Hermann | 366/339 |
| 3,923,288 | 12/1975 | King | 366/336 |
| 4,014,463 | 3/1977 | Hermann . | |
| 4,050,676 | 9/1977 | Morishina et al. | 366/339 |
| 4,183,682 | 1/1980 | Lieffers | 366/339 |
| 4,207,009 | 6/1980 | Glocker | 366/340 |

OTHER PUBLICATIONS

"Kenpac Fail-Safe Mixer/Applicator for Production Assembly or Field Repairs", commercial literature of the Kenics Corporation.

Primary Examiner—Robert W. Jenkins
Attorney, Agent, or Firm—Donald M. Sell; James A. Smith; David R. Cleveland

[57] ABSTRACT

A multiple-barreled resin dispensing device having a syringe, an exit conduit, a static mixing element, means for detachably coupling the inlet of the exit conduit to the outlet end of the syringe, and means for locating the static mixing element within the exit conduit to provide rotational alignment of the static mixing element relative to the syringe.

5 Claims, 10 Drawing Figures

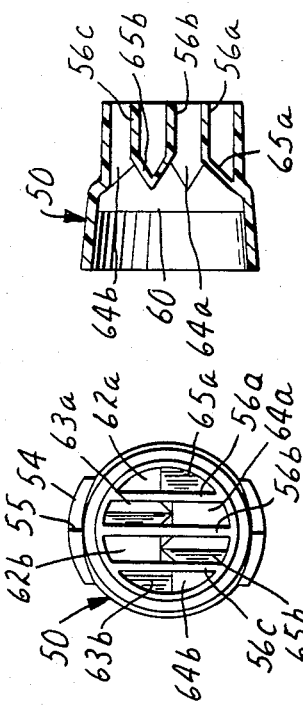
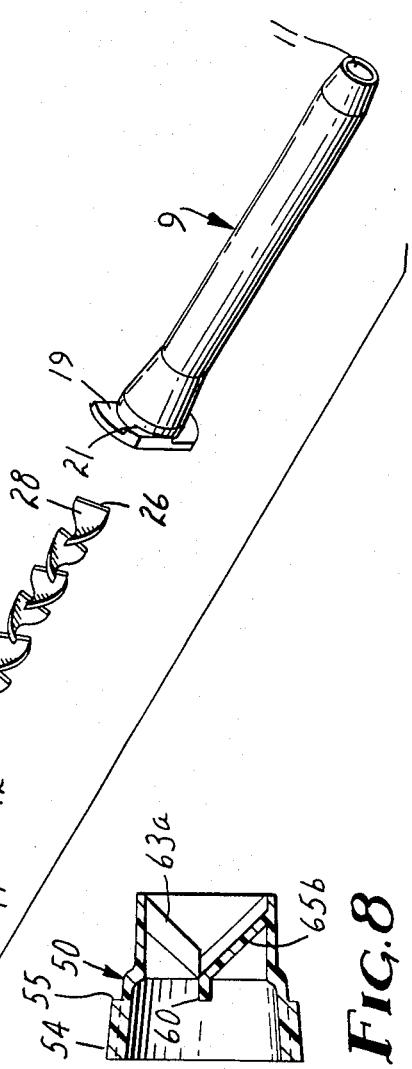
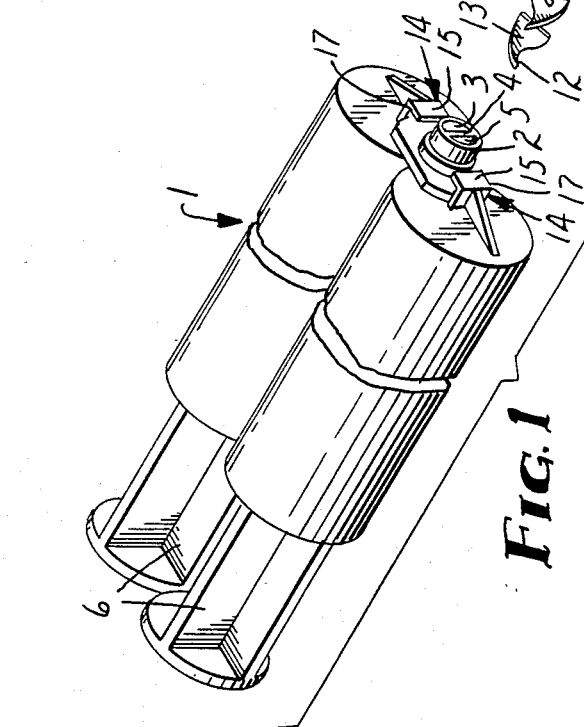
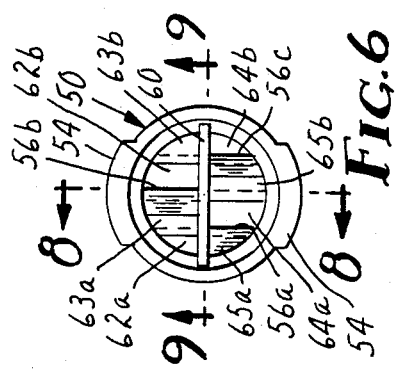

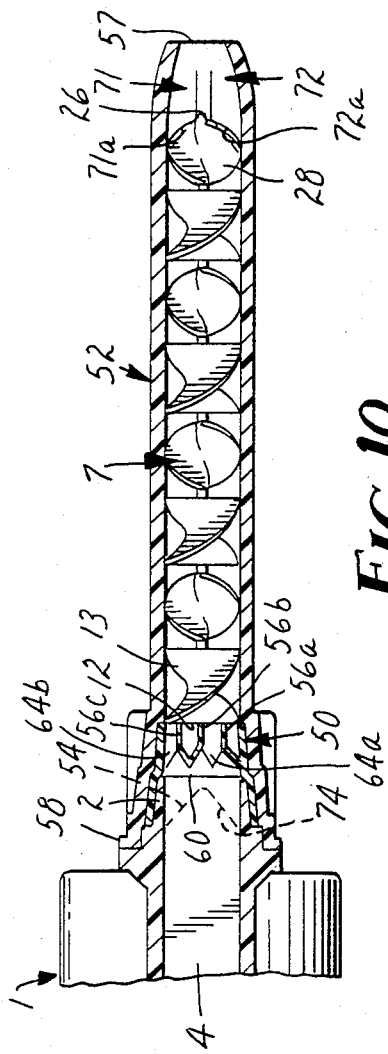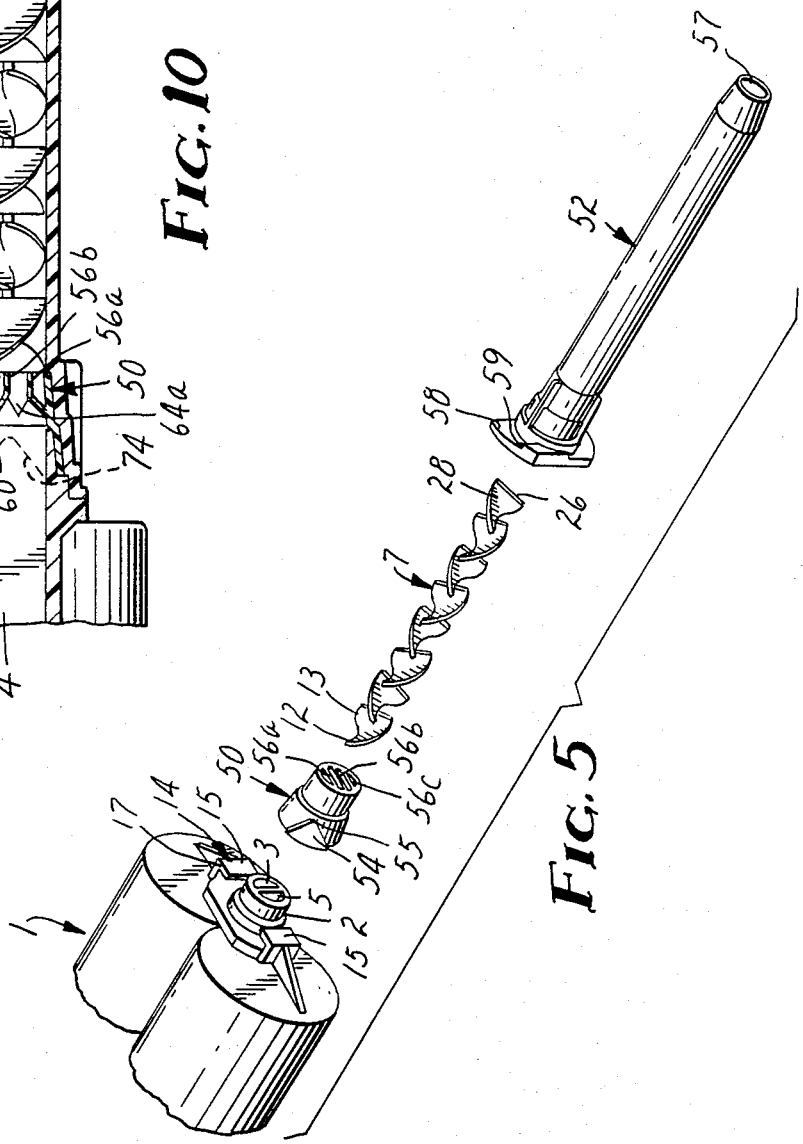

STATIC MIXING DEVICE

TECHNICAL FIELD

This invention relates to mixing devices for polymerizable resins. This invention also relates to disposable nozzles for such mixing devices.

BACKGROUND ART

Multiple-part curable resins (e.g., epoxides and dental restorative resins) frequently are dispensed and mixed using a multiple-barrelled syringe equipped with an exit nozzle containing a static mixing element. The materials contained in the syringe are dispensed and mixed by depressing the syringe plunger, thereby forcing the resin components from the syringe barrels into the static mixing element (where the resin parts are intermixed with one another) and out the exit nozzle. When it is contemplated that the contents of the syringe will not be completely consumed in one use, the static mixing element and exit nozzle frequently are designed to be detached from the syringe outlet and disposed of after use. In such applications, several detachable and disposable static mixing elements and exit nozzles ordinarily are included with each syringe. After a quantity of curable resin has been dispensed and mixed from the syringe, the used static mixing element and exit nozzle can be detached from the syringe outlet and discarded, and a new static mixing element and exit nozzle fitted to the syringe outlet.

One commercially used double-barrelled dispensing device employs a static mixing element made from a plurality of counter-rotated "bow-tie" or auger-like mixing blades of the type described in U.S. Pat. Nos. 3,286,992 and 3,664,638. Such a static mixing element successively subdivides, rotates, and recombines the incoming resin streams to convert them to a homogeneous, readily curable mass. This dispensing device is referred to by its manufacturer as a "Kenpac" syringe and is described in "Kenpac fail-safe mixer/applicator for production assembly or field repairs", commercial literature of the Kenics Corporation. The "Kenpac" syringe has two barrels, each having a capacity of about 12 cm$^3$. A disposable eightbladed static mixing element about 6 mm in diameter by about 50 mm long is used with the syringe, together with an exit nozzle which encases the static mixing element and detachably mounts on the syringe outlet. If the degree of mixing offered by the use of a single static mixing element and nozzle is insufficient, additional static mixing elements can be interposed between the exit nozzle and syringe outlet, and are carried in nozzle extension tubes. After use of a portion of the syringe's contents, the used static mixing element(s), exit nozzle, and nozzle extension tubes (if any) can be removed from the syringe outlet and replaced with new components.

DISCLOSURE OF INVENTION

A shortcoming of the above-described commercial syringe assembly is that the static mixing element is not fixed in rotational relationship to the syringe unit. When the two resins contained in the syringe are expelled from the syringe, two contiguous streams of resin, in the form of a coextruded two-layered mass, pass from the syringe barrel through the syringe outlet and toward the static mixing element. When the two resin streams impinge upon the first mixing blade of the static mixing element, the incoming streams are supposed to be split or subdivided into a mass containing two new streams of resin, each new stream containing one-half of each of the two incoming streams. Ideal mixing would occur if the inlet end of the first mixing blade of the static mixing element were perpendicular to the plane of contiguity between the two incoming resin streams. When so oriented, the mixing blade will evenly subdivide the incoming resin streams to direct one-half of each incoming stream into each new stream. In practice however, the static mixing element has a random orientation with respect to the incoming resin streams, and the first mixing blade of the static mixing element usually does not lie in an ideal relationship with respect to the incoming resin streams. In fact, when the first mixing blade of the static mixing element is located parallel to the plane of contiguity of the incoming resin streams, then the first mixing blade of the static mixing element is essentially ineffective in subdividing the resin streams, and serves only to impart a rotational displacement to the resin streams as they pass through the first mixing stage of the static mixing element. On average, the first mixing blade of such a dispensing device is oriented at a position yielding about 50 percent of maximum effectiveness for the first mixing stage of the static mixing element.

The present invention provides a resin dispensing device, comprising:

(a) a multiple-barreled syringe having an outlet through which can flow resin streams with a plane of contiguity between adjacent resin streams;

(b) an exit conduit comprising a generally cylindrical bore with an inlet end and an outlet end, said cylindrical bore being adapted to contain a static mixing element and prevent expulsion of said static mixing element from said outlet end of said conduit when polymerizable resin is forced therethrough;

(c) a static mixing element located in the bore of said exit conduit, said element comprising multiple counter-rotated auger-like mixing blades and an inlet end edge on the mixing blade proximate the inlet end of said conduit;

(d) means for detachably coupling said inlet end of said conduit to said syringe outlet; and (e) means for orienting said inlet end edge perpendicular to said plane of contiguity between said resin streams.

BRIEF DESCRIPTION OF DRAWING

A preferred embodiment of the invention is illustrated in the accompanying drawing, in which:

FIG. 1 is an exploded view in perspective of a syringe, static mixing element, and exit conduit of this invention;

FIG. 5 is an exploded view in perspective of another embodiment of this invention, in which a premix chamber is employed;

FIG. 6 is an inlet and view of the premix chamber of FIG. 5;

FIG. 7 is outlet end view of the premix chamber of FIGS. 5 and 6;

FIG. 8 is a sectional view of the premix chamber of FIGS. 5–7, sectioned along line 8–8' of FIG. 6;

FIG. 9 is a sectional view of the premix chamber of FIGS. 5–8, sectioned along line 9–9' of FIG. 6; and FIG. 10 is a sectional view of a portion of the embodiment of FIG. 5 in assembled form.

DETAILED DESCRIPTION

Figure 2:
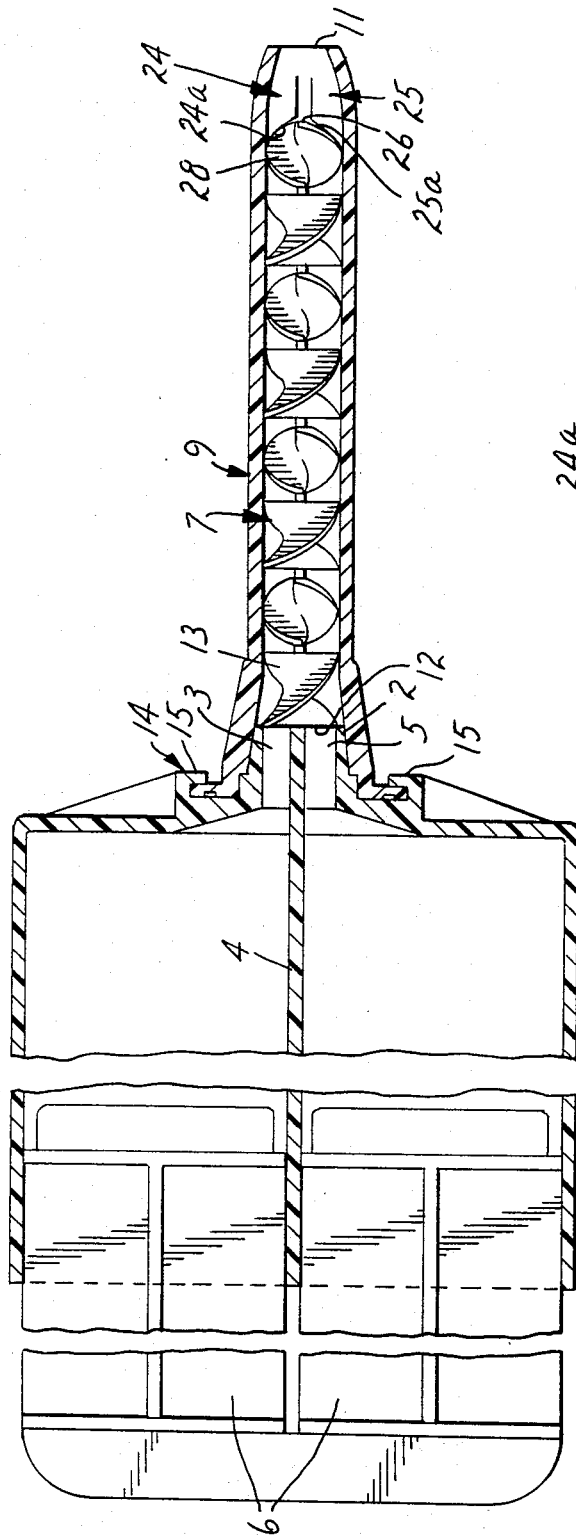
FIG. 2 is a cross-sectional view of the syringe assembly of FIG. 1 in assembled form.

Referring now to FIG. 1, there is shown an exploded view in perspective of a static mixing device of this invention. Syringe 1 has two parallel internal chambers, each of which is intended to be filled with one part of a two-part polymerizable material, e.g., polymerizable resin. The chambers in syringe 1 are separated by barrier 4. When a pair of plungers 6 are forced into the chambers in syringe 1, the contents of the syringe exit via outlet 2 through outlet passages 3 and 5, flow through static mixing element 7 and exit conduit 9, and are intimately mixed to form a homogeneous mass which will rapidly polymerize following expulsion from outlet 11 of exit conduit 9. Static mixing element 7 is prevented from being expelled during use from the outlet end of exit conduit 9 by a suitable constriction in the inside diameter of exit conduit 9 proximate its outlet end.

In this invention, maximum efficiency of mixing is obtained by insuring that the inlet end 12 of the first mixing blade 13 of static mixing element 7 is generally perpendicular to the plain of contiguity between the two resin streams exiting syringe 1 through exit passages 3 and 5. Such perpendicular orientation is obtained using a locating tang (shown in more detail in FIGS. 2–4 below) in exit conduit 9, which locating tang serves to orient static mixing element 7 with respect to syringe 1.

Rotational alignment of exit conduit 9 with respect to syringe 1 is obtained using a suitable mounting means (e.g., a bayonet mount). Bayonet locking tabs 14 have locking prongs 15 and stop surfaces 17. Exit conduit 9 has locking ramps 19 and stop surfaces 21. Exit conduit 9 is mounted on syringe 1 by centering the inlet of exit conduit 9 over outlet 2 of syringe 1, while aligning exit conduit 9 so that it can be pushed between bayonet locking tabs 14. Exit conduit 9 is then inserted firmly over outlet 2, and rotated approximately 90° clockwise (as viewed from the exit end of the conduit) so that locking ramps 19 are wedged between locking prongs 15 and the main body of syringe 1, and stop surfaces 17 engage stop surfaces 21.

When so mounted, exit conduit 9 is fixably rotationally aligned with respect to syringe 1. In addition, through locating means described in more detail below, static mixing element 7 is fixably rotationally aligned with respect to exit conduit 7 and syringe 1. Static mixing element 7 and exit conduit 9 are firmly attached to syringe 1, but can be readily removed and discarded after use by rotating exit conduit 9 approximately 90° counterclockwise (as viewed from the exit end of the conduit) and pulling exit conduit 9 away from syringe 1.

In FIG. 2 there is shown a sectional view of the syringe assembly of FIG. 1 in assembled form. Syringe 1, exit nozzle 2, exit passages 3 and 5, barrier 4, plungers 6, static mixing element 7, exit conduit 9, inlet edge 12, first mixing blade 13, bayonet locking tabs 14, and locking prongs 15 are as in FIG. 1. Static mixing element 7 is rotationally aligned within exit conduit 9 by one or more guides (two guides, numbered 24 and 25, are shown) proximate the outlet end of exit conduit 9.

Guides 24 and 25 are small inward projections in the bore of exit conduit 9, and have a "fish mouth" appearance when viewed in perspective. When viewed in isolation, locking guides 24 and 25 each resemble the nib of a fountain pen.

When static mixing element 7 is inserted into the inlet end of exit conduit 9, and pushed toward the outlet end of exit conduit 9, guides 24 and 25 serve to rotationally align static mixing element 7 within exit conduit 9. When leading edge 26 of the final mixing blade 28 of static mixing element 7 approaches the outlet end of exit conduit 9, guides 24 and 25 cause static mixing element 7 to rotate about its long axis until leading edge 26 abuts edge surface 24a of guide 24 or or edge surface 25a of guide 25.

Figure 3:
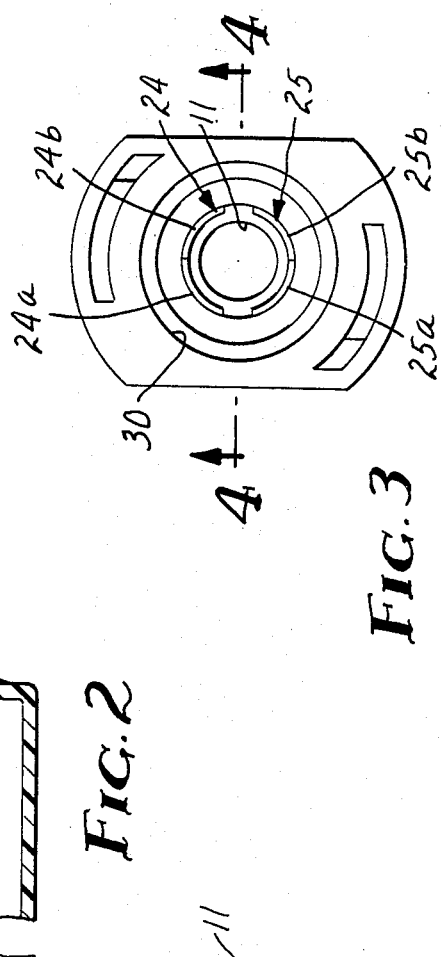
FIG. 3 is an inlet end view of the exit conduit of FIGS. 1 and 2.

In FIG. 3 is shown an inlet end view of exit conduit 9 of FIGS. 1 and 2. In this view, inlet 30 of the cylindrical bore of exit conduit 9 can be seen, along with outlet 11 of exit conduit 9. Guides 24 and 25 project only a small distance into the interior of the cylindrical bore in exit conduit 9. Edge surfaces 24a and 24b on guide 24 and edge surfaces 25a and 25b on guide 25 serve to twist the leading edge 26 of static mixing element 7 into proper abutting relationship with guides 24 and 25, thereby providing correct rotational alignment of static mixing element 7 with respect to exit conduit 9. Orientation of exit conduit 9 with syringe 1 (e.g., through use of the bayonet lock shown in FIGS. 1–3) provides rotational alignment of static mixing element 7 with the two streams of resin passing through outlet 2 of syringe 1.

Figure 4:
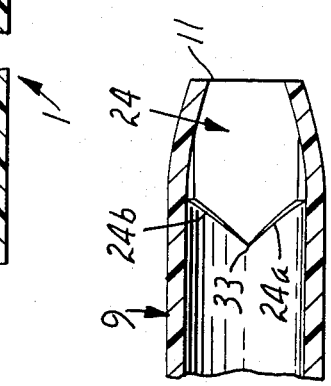
FIG. 4 is a sectional view of a portion of the outlet end of the exit conduit of FIGS. 1–3, sectioned along line 4-4' of FIG. 3.

In FIG. 4 is shown a sectional view of a portion of the outlet end of exit conduit 9 of FIGS. 1–3, sectioned along line 4–4' of FIG. 3. Outlet 11 is as in FIGS. 1–3. The nib-like shape of guide 24 can be seen clearly in FIG. 4. Edge surfaces 24a and 24b intersect at cusp 33. When a static mixing element is inserted sufficiently far into exit conduit 9 to strike cusp 33, the leading edge of the static mixing element is deflected by cusp 33 toward edge surface 24a or toward edge surface 24b, thereby providing the desired rotational alignment. Depending upon whether the static mixing element abuts against edge surface 24a or 24b of guide 24 (and against corresponding edge surface 25b or 25a of guide 25), the final orientation of the static mixing element will be in one of two positions, each of those positions being 180° of rotation apart from the other. Each position is equally acceptable as a means for optimizing the efficiency of the first blade of the static mixing element, since in either position the first mixing element will intersect the incoming streams of resin at an approximate right angle to the plane of contiguity between the incoming streams and subdivide the incoming streams equally.

FIGS. 5–10 illustrate another embodiment of this invention, in which a premix chamber is employed. The premix chamber splits the two streams of resin exiting from the syringe into four or more parallel streams (an embodiment providing four streams is shown) of resin. These four parallel streams of resin are then allowed to pass through the static mixing element for further mixing. It has been found that the use of such a premix chamber in combination with the eight-stage static mixing element 7 shown in the drawing provides especially thorough mixing. Use of the premix chamber therefore provides good mixing of highly viscous materials (e.g., silicone dental impression resins) while minimizing the amount of entrained resin left in the static mixing element and premix chamber after use, thereby minimizing waste of resin.

Referring now to FIG. 5, there is shown an exploded view in perspective of a static mixing device of this invention having a premix chamber. Syringe 1 and static mixing element 7 are the same as the syringe and static mixing element of FIGS. 1–4. Premix chamber 50 has a larger diameter at its inlet end than at its outlet end, in order to assure proper insertion by the user of premix chamber 50 in exit conduit 52. Locating tangs 54 and cusps 55 (only one of each is shown) provide correct rotational alignment of premix chamber 50 with respect to exit conduit 52 and the outlet of syringe 1. Barriers 56a, 56b and 56c separate the four streams of resin which will exit through premix chamber 50. Exit conduit 52 has outlet 57, locking ramps 58, and stop surfaces 59.

Assembly of the parts shown in FIG. 5 is carried out by inserting static mixing element 7 and premix chamber 50 into exit conduit 52. Static mixing element 7 is urged into proper rotational alignment with syringe 1 and premix chamber 50 by guides (not shown in FIG. 5) within exit conduit 9 proximate outlet 57. Premix chamber 50 is urged into proper rotational alignment with syringe 1 and static mixing element 7 by recesses (not shown in FIG. 5) located in the bore of exit conduit 52 proximate the inlet end of exit conduit 52. These recesses engage tangs 54 and cusps 55 on premix chamber 50. Exit conduit 52 is mounted on syringe 1 by centering the inlet of exit conduit 52 over outlet 2 of syringe 1, while aligning exit conduit 52 so that it can be pushed between bayonet locking tabs 14. Exit conduit 52 is then inserted firmly over outlet 2, and rotated approximately 90° clockwise (as viewed from the inlet end of the conduit) so that locking ramps 58 are wedged between locking prongs 15 and the main body of syringe 1, and stop surfaces 17 engage stop surfaces 59.

When so mounted, syringe 1, premix chamber 50, and static mixing element 7 are correctly rotationally aligned with respect to one another. When the plungers in syringe 1 are depressed, two streams of polymerizable resin flow through outlet 2 of syringe 1 and into premix chamber 50. Premix chamber 50 splits the two streams of incoming resin into four parallel streams, whereupon the four streams then pass through static mixing element 7 and exit conduit 52, exiting through outlet 57 as a well-mixed homogeneous mass. The rotational alignment of premix chamber 50 and first mixing blade 13 of static mixing element 7 insures that the four parallel streams of polymerizable resin exiting premix chamber 50 are evenly subdivided by first mixing blade 13 of static mixing element 7, and mixed with maximum efficiency.

In FIG. 6 there is shown an inlet end view of premix chamber 50. Both tangs 54 can be seen. Separator 60 splits the incoming mass of resin in half. In use, separator 60 is aligned with separator 4 of syringe 1 so that both separator 60 and separator 4 are in the same plane. When so aligned, separator 60 is in the plane of contiguity between the two streams of polymerizable resin exiting syringe 1, and serves to deflect one stream to one side of separator 60, while deflecting the other stream to the opposite side of separator 60. In the view shown in FIG. 6, one stream would pass below separator 60, while the other stream would pass above separator 60.

The stream of resin passing below separator 60 flows through openings 64a and 64b, and is deflected into those openings by barriers 65a and 65b. After flowing through openings 64a and 64b, the streams expand in cross-sectional area and occupy the spaces behind barriers 63a and 63b (the word "behind" refers to the region proximate the outlet end of the chamber).

The stream passing above separator 60 flows into openings 62a and 62b, and is deflected into those openings by barriers 63a and 63b. After passing through opening 62a and 62b, the streams then expand in cross-sectional area, and occupy the spaces behind barriers 65a and 65b.

In this fashion, the two streams of resin flowing into the inlet end of premix chamber 50 are divided into four parallel, alternating streams of resin at the outlet end of premix chamber 50. The plane of contiguity of the two incoming resin streams is perpendicular the three parallel planes of contiguity of the four exiting resin streams.

In FIG. 7 is shown an outlet end view of premix chamber 50. The respective identifying numbers in FIG. 7 are the same as in FIGS. 5 and 6. The manner in which resin flows through opening 62a, 62b, 64a, and 64b and increases in cross-sectonal area to occupy the spaces behind (i.e., toward the outlet end of premix chamber 50) respective barriers 65a, 65b, 63a, and 63b can be seen in greater detail.

In FIG. 8 is shown a sectional view of premix chamber 50, sectioned along line 8–8' of FIG. 6. Resin flowing below separator 60 is blocked by barrier 65b and flows into the openings on either side of barrier 65b (these openings are not shown in FIG. 8, but are numbered 64a and 64b in FIGS. 6 and 7). Resin flowing above separator 60 is blocked by barrier 63b (not shown in FIG. 8) and barrier 63a, and flows through openings (not shown in FIG. 8) 62a and 62b.

In FIG. 9 is shown a sectional view of premix chamber 50, sectioned along line 9–9' of FIG. 6. Resin flowing past the visible surface of separator 60 is blocked by barriers 65a and 65b, and flows through openings 64a and 64b.

In FIG. 10 is shown a sectional view of a portion of the syringe assembly of FIG. 5 in assembled form. The desired rotational alignment of syringe 1, static mixing element 7, and premix chamber 50 is provided by guides 71 and 72 (whose edge surfaces 71a and 72a guide leading edge 26 of final mixing blade 28 into proper rotational alignment with the remaining components of the syringe assembly) and by recess 74 (shown in phantom) in exit conduit 52, into which recess fits tang 54 of premix chamber 50.

In the various embodiments shown in the Drawing arrow- or nib-shaped locating guides or tangs are employed in one or both ends of the exit conduit to properly align the static mixing element (and premix chamber, if employed) with the remaining components of the syringe assembly. Other shapes for the locating guides or tangs can be used, as will be apparent to those skilled in the art of mechanical design. If desired, the static mixing element (and premix chamber, if employed) can be rotationally aligned with respect one another and to the syringe using other orienting means. For example, the exit face of the syringe outlet can be dished or formed into a trough having sloping sides, with the bottom of the trough being perpendicular to the separator between the syringe chambers. The exit conduit can then be designed with an appropriate length such that forcing the exit conduit over the syringe will cause the first blade of the static mixing element to be urged into correct rotational alignment with respect to the syringe so that the leading edge of the first mixing stage of the static mixing element lies in the bottom of the trough in the exit face of the syringe outlet. In such case, locating tangs at the outlet end of the exit conduit will not be required, but can be used if desired. The premix chamber can be provided with a protrusion at its inlet end and which matches such a trough, thereby causing the premix chamber to be urged into proper rotational alignment with the syringe, and the outlet face of the premix chamber can be provided with a trough, the bottom of which is perpendicular to the planes defined by the separators in the premix chamber, thereby causing the static mixing element to be urged into correct rotational alignment with respect to the syringe and premix chamber.

If desired, extension tubes (which can themselves be regarded as exit conduits) can be attached to the exit conduits shown in the Drawing, thereby enabling the use of additional static mixing elements on the syringe assembly, to provide a longer train of mixing blades and more complete mixing. When such extension tubes are used, they should be provided with suitable guides or other rotational alignment means to preserve fixed rotational alignment of the static mixing element within the extension tube and with respect to parts upstream (e.g., syringe, premix chamber, and any upstream static mixing elements) and parts downstream (e.g., the exit conduit, and any downstream static mixing elements or additional extension tubes).

The bayonet mount shown in the Drawing is a convenient means for detachably coupling the exit conduit and syringe. However, other coupling means providing suitable rotational alignment between syringe and exit conduit can be used, e.g., threaded connections, frictional connections having a non-circular cross-section, splined or keyed fittings, and the like. If the means for aligning the static mixing element and syringe is independent of exit conduit orientation (e.g., if the above-described trough-shaped syringe outlet is employed), then the means for detachably coupling the exit conduit and syringe need not also provide rotational orientation of exit conduit and syringe. In such case, a simple snap-fit coupling, circular in cross-section, can be used between exit conduit and syringe. As will be appreciated by those skilled in the art, other connections can be substituted for such snap-fit coupling if desired.

As will also be appreciated by those skilled in the art, the cross-sectional area of the respective syringe barrels or syringe outlet can be varied to provide the desired mixing ratio for the syringe components. In addition, additional barrels can be provided for mixing compositions having more than two components (e.g., three components), and in such case the teachings of this invention can be employed to assure optimum alignment of the static mixing element with the incoming resin streams. In the latter instance, the syringe barrels preferably are aligned so that their central axes are in the same plane, and the streams of resin exiting the syringe have parallel planes of contiguity between adjacent resin streams.

The contents of the syringe can be sealed prior to use by placing plunger seals (and plungers, if desired) in the open ends of the syringe barrels. The syringe outlet can be sealed by providing a snip-off plastic molding at the outlet end of the syringe. Alternatively, and preferably, the outlet end of the syringe is sealed with a removable cap equipped with an appropriate locking mechanism. If the exit conduit is attached to the syringe using a bayonet mount, it is preferable to employ a similar bayonet mount on the removable cap. Such a cap can then be reinstalled on the syringe between uses thereof.

Various modifications and alterations of this invention will be apparent to those skilled in the art without departing from the scope and spirit of this invention and the latter should not be restricted to that set forth herein for illustrative purposes.

What is claimed is:

1. A resin dispensing device, comprising:
   (a) a multiple-barrelled syringe having an outlet through which can flow resin streams with a plane of contiguity between adjacent resin streams;
   (b) an exit conduit comprising a generally cylindrical bore with an inlet end and an outlet end, said cylindrical bore being adapted to contain a static mixing element and prevent expulsion of said static mixing element from said outlet end of said conduit when polymerizable resin is forced therethrough;
   (c) a static mixing element located in the bore of said exit conduit, said element comprising multiple counter-rotated auger-like mixing blades and an inlet end edge on the mixing blade proximate the inlet end of said conduit;
   (d) means for detachably coupling said inlet end of said conduit to said syringe outlet; and
   (e) means for orienting sid inlet end edge perpendicular to said plane of contiguity between said resin streams, said orienting means being in the form of one or more tangs which abut said static mixing element proximate said outlet end of said exit conduit.

2. A resin dispensing device, comprising:
   (a) a multiple-barrelled syringe having an outlet through which can flow resin streams with a plane of contiguity between adjacent resin streams;
   (b) an exit conduit comprising a generally cylindrical bore with an inlet end and an outlet end, said cylindrical bore being adapted to contain a static mixing element and prevent expulsion of said static mixing element from said outlet end of said conduit when polymerizable resin is forced therethrough;
   (c) a static mixing element located in the bore of said exit conduit, said element comprising multiple counter-rotated auger-like mixing blades and an inlet end edge on the mixing blade proximate the inlet end of said conduit;
   (d) means for detachably coupling said inlet end of said conduit to said syringe outlet; and
   (e) means for orienting said inlet end edge perpendicular to said plane of contiguity between said resin streams, said orienting means being in the form of a trough with sloping sides in the exit face of said syringe outlet.

3. A resin dispensing device, comprising:
   (a) a multiple-barrelled syringe having an outlet through which can flow resin streams with a plane of contiguity between adjacent resin streams;
   (b) an exit conduit comprising a generally cylindrical bore with an inlet end and an outlet end, said cylindrical bore being adapted to contain a static mixing element and prevent expulsion of said static mixing element from said outlet end of said conduit when polymerizable resin is forced therethrough;
   (c) a static mixing element located in the bore of said exit conduit, said element comprising multiple counter-rotated auger-like mixing blades and an inlet end edge on the mixing blade proximate the inlet end of said conduit;
   (d) means for detachably coupling said inlet end of said conduit to said syringe outlet; and (e) means for orienting said inlet end edge perpendicular to said plane of contiguity between said resin streams, wherein said exit conduit is fixably rotationally aligned with respect to said syringe and said static mixing element is fixedly rotationally aligned with respect to said exit conduit.

4. A resin dispensing device, comprising:
(a) a multiple-barrelled syringe having an outlet through which can flow resin streams with a plane of contiguity between adjacent resin streams;
(b) an exit conduit comprising a generally cylindrical bore with an inlet end and an outlet end, said cylindrical bore being adapted to contain a static mixing element and prevent expulsion of said static mixing element from said outlet end of said conduit when polymerizable resin is forced therethrough;
(c) a static mixing element located in the bore of said exit conduit, said element comprising multiple counter-rotated auger-like mixing blades and an inlet end edge on the mixing blade proximate the inlet end of said conduit;
(d) means for detachably coupling said inlet end of said conduit to said syringe outlet; and
(e) means for orienting said inlet end edge perpendicular to said plane of contiguity between said resin streams;

said device further comprising a premix chamber proximate said syringe outlet and within said exit conduit, said syringe having two barrels each containing resin, said barrels being separated by a barrier, and said premix chamber splitting streams of resin exiting from said two barrels into four or more streams of resin with parallel planes of contiguity between streams.

5. An exit conduit for attachment to a resin dispensing device comprising a multiple-barrelled syringe having an outlet through which can flow resin streams with a plane of contiguity between adjacent resin streams, said exit conduit comprising a generally cylindrical bore with an inlet end and an outlet end, said cylindrical bore being adapted to contain and retain a static mixing element comprising multiple counter-rotated auger-like mixing blades with an inlet end edge on the mixing blade proximate the inlet end of said conduit, said exit conduit having means for orienting said inlet end edge perpendicular to said plane of contiguity between said resin streams, said orienting means being in the form of one or more tangs which project inwardly from said cylindrical bore and abut said static mixing element proximate said outlet end of said exit conduit.

* * * * *

UNITED STATES PATENT AND TRADEMARK OFFICE
CERTIFICATE OF CORRECTION

PATENT NO. : 4,538,920

DATED : September 3, 1985

INVENTOR(S) : Gerald E. Drake

It is certified that error appears in the above-identified patent and that said Letters Patent is hereby corrected as shown below:

Column 4, line 14, "or or edge" should read -- or edge --.

Column 8, line 24 "sid" should read -- said --.

Column 9, line 6, "fixedly" should read -- fixably --.

Signed and Sealed this

Twenty-seventh Day of May 1986

[SEAL]

Attest:

DONALD J. QUIGG

Attesting Officer

Commissioner of Patents and Trademarks